United States Patent [19]

West et al.

[11] Patent Number: 5,508,304
[45] Date of Patent: Apr. 16, 1996

[54] GLUCAGON ANTAGONISTS AND METHODS RELATING THERETO

[75] Inventors: Robert R. West, Seattle; Virender Labroo, Mill Creek; James R. Piggott, Bothell; Robert A. Smith, Seattle; Patricia A. McKernan, Woodinville, all of Wash.

[73] Assignee: ZymoGenetics, Inc., Seattle, Wash.

[21] Appl. No.: 288,875

[22] Filed: Aug. 10, 1994

Related U.S. Application Data

[63] Continuation of Ser. No. 995,375, Dec. 23, 1992, abandoned.

[51] Int. Cl.$^6$ ............................................. A61K 31/21
[52] U.S. Cl. ............................................. 514/510
[58] Field of Search ........................ 514/510; 435/118, 435/254

[56] References Cited

FOREIGN PATENT DOCUMENTS 2029993  5/1991  Canada.

OTHER PUBLICATIONS

Ueno, Y., *Mycotoxins–Production, Isolation, Separation and Purification*, V. Betina (Editor), 1984, Elsevier Science Publishers B.V., Amsterdam.
Stark, A. A., et al. *Journal of Environmental Pathology & Toxicology*, 2:313–324, 1978.
Cameron, Donald W., et al., *Aust. J. Chem.*, 29:1535–1548, 1976.
Pal, Tarasankar and Anjali Pal, *J. Indian Chem. Soc.*, 66: 236–238, 1989.
Franck, Bruchard, et al., *Angew. Chem. Internat.*, 14:819–820, 1975.
Betina, Vladimir and Stefan Kuzela, *Chem.–Biol. Interactions*, 62:179–189, 1987.
Yanagi, Yoshikazu, et al., *J. Pesticide Sci.*, 1:107–114, 1976.
Kawai, Kiyoshi, et al., *Toxicology Letters*, 20:155–160, 1984.
Santesson, Johan, *Acta Chem. Scand.*, 24(9):3331–3334, 1970.
Gill, Melvyn and Alberto Gimenez, *Phytochemistry*, 30(3):951–955, 1991.
Hatfield, George M. and Daniel E. Slagle, *Journal Lloydia*, 36(3):354–356 (1980).
Shibata, Shoji, et al., *Journal Chem. Pharm. Bull.*, 3:278–283, 1955.
Shibata, Shoji, et al., *Journal Chem. Pharm. Bull.*, 6 573–575, 1957.
Kawai, K., et al., *Proc. Jpn. Assoc. Mycotoxicol.*, 19:25–29, 1984.
Podojil, M., et al., *Folia Microbiol.*, 23:438–443, 1979.
Mori, Hideki, et al., *Cancer Research*, 44:2918–2923, 1984.
Kawai, Kiyoshi, et al., *Toxicology Letters*, 20:155–160, 1984.
Nikaido, Tamotsu, et al., *Chem. Pharm. Bull.*, 32(8):3075–3078, 1984.
Dobias, Jozef, et al., *Biologia [Bratislava]*, 35(6),431–434, 1980.
Kawai, K., et al., *Proc. Jap. Assoc. Mycotoxicol.*, 15:19–21, 1982.
Stark et al., "Mutagenicity and Antibacterial Activity of Mycotoxins Producted by Panicillium Islandicum Sopp and Penicillim Rugulosom," *J. of Environ. Path. Toxicol.* 2(2):313–324, 1978.
Betina et al., "Uncoupling Effect of Fungal Hydroxyanthraquinones on Mitochondrial Oxidative Phosphorylation," *Chemico–Biological Interactions* 62(2):179–189, 1987.
Derwent Abstract AN 81–48493 (JP 56–055334) May 1981.
Roane et al., Chem. Abs, 91:153952r, 1979.
Yanagi et al., Biol. Abs, 63(9):50978, 1976.
Cho et al., Biol. Abs, 90(9):98361, 1990.

*Primary Examiner*—Raymond Henley, III
*Assistant Examiner*—Kevin E. Weddington
*Attorney, Agent, or Firm*—Karl R. Hermanns; Seed and Berry

[57] ABSTRACT

Glucagon antagonists and methods relating thereto are disclosed. The glucagon antagonists include skyrin and skyrin analogs, and serve to inhibit the stimulation of a glucagon-induced response pathway, such as the adenylate cyclase response pathway or the inositol phosphate response pathway. The glucagon antagonists may be used within therapeutic compositions to treat disease states associate with elevated glucose levels, including diabetes and hyperglycemia. The present invention also discloses a biologically pure culture of ATCC accession number 74200, as well as methods relating to the production of glucagon antagonists by cultivating the same in a nutrient medium and recovering the glucagon antagonist therefrom.

4 Claims, 8 Drawing Sheets

PURIFICATION FLOW CHART

GLUCAGON ANTAGONISTS AND METHODS RELATING THERETO

CROSS-REFERENCE TO RELATED APPLICATION

This application is a continuation of U.S. application Ser. No. 07/995,375 filed Dec. 23, 1992, now abandoned.

TECHNICAL FIELD

This application is generally directed to glucagon antagonists, and more specifically to the use of skyrin and skyrin analogs as glucagon antagonists.

BACKGROUND OF THE INVENTION

Human diabetes, a disease in which a major indicator is an elevated blood glucose level, is generally believed to result from low insulin levels and elevated glucagon levels. However, hyperglycemia in non-insulin dependent diabetes (both in non-obese and obese patients), has been shown in the presence of both elevated glucagon and insulin levels.

Insulin is known to rapidly decrease blood glucose levels, while glucagon (a polypeptide hormone twenty-nine amino acid residues in length) is believed to contribute to elevated blood glucose levels by binding to liver membrane receptors, and thereby triggering glycogenolysis which results in the production of glucose. Elevated glucagon levels are also associated with a substantial increase in gluconeogenesis.

The binding of glucagon to its cellular receptor triggers the stimulation of adenylate cyclase activity leading to the production of cyclic AMP (cAMP), and results in an increase in glycogenolysis and gluconeogenesis and the accompanying release of glucose. In addition to cAMP-stimulated gluconeogenesis and glycogenolysis, other pathways have been suggested for the glucagon-stimulated production of glucose through glycogeaolysis and gluconeogenesis. For example, the binding of glucagon to its cellular receptor activates protein kinase C leading to the formation of inositol triphosphate, which acts as a signal for the release of free calcium sequestered in the endoplasmic recticulum (Pittner and Fain, *Biochem. J.* 277:371–378, 1991). Furthermore, Wakelam et al. (*Nature* 323:68–71, 1986) suggest that the stimulation of inositol triphosphate production provides a cAMP-independent pathway for gluconeogenesis and glycogenolysis.

While stable control of insulin levels is difficult to achieve, treatment for insulin-dependent diabetes and some non-insulin dependent diabetes has been achieved through a combination of controlled diet and periodic doses of exogenous insulin. It is believed that the therapeutic use of glucagon antagonists will inhibit glycogenolysis and help to lower and/or maintain blood glucose levels in diabetics by inhibiting glucagon-induced glucose production.

Accordingly, it is an object of the present invention to provide glucagon antagonists, as well as methods for the production thereof. It is a further object of this invention to provide methods of formulating and administering glucagon antagonists to treat disease states associated with elevated glucose levels. The present invention fulfills these objectives, and provides further related advantages.

SUMMARY OF THE INVENTION

Briefly stated, the present invention discloses glucagon antagonists, as well as methods of production and administration of glucagon antagonists. More specifically, the glucagon antagonists of this invention are skyrin and skyrin analogs, such as oxyskyrine.

In one embodiment, a method for inhibiting the stimulation of a glucagon-induced response pathway in a warm-blooded animal is disclosed. In this method, a pharmaceutically effective amount of a composition containing the glucagon antagonist and a pharmaceutically acceptable carrier or diluent is administered to the animal.

In a further embodiment, a method is disclosed for lowering or maintaining blood glucose levels in a patient by administering to the patient a pharmaceutically effective amount of a composition containing the glucagon antagonist and a pharmaceutically acceptable carrier or diluent.

In yet a further embodiment, the present invention is directed to a biologically pure culture deposited on Dec. 22, 1993 (isolate Z-522) under ATCC accession number 74200 (American Type Culture Collection, 12301 Parklawn Drive, Rockville, Md. 20852), as well as a method for producing a glucagon antagonist by cultivating the same in a nutrient medium and recovering the glucagon antagonist from the medium.

These and other aspects of this invention will become evident upon reference to the following detailed description and attached drawings.

DETAILED DESCRIPTION OF THE INVENTION

Figure 1:
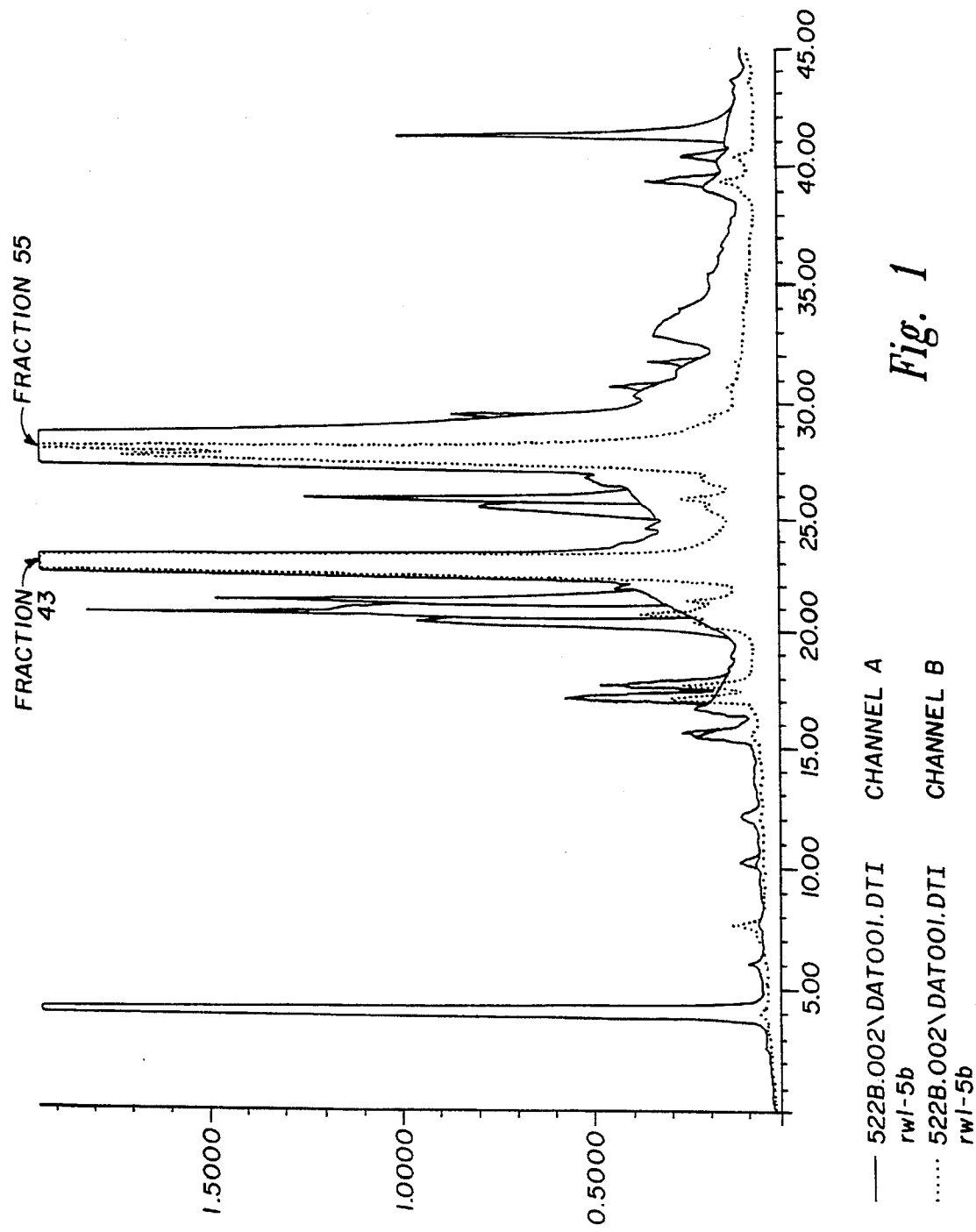
FIG. 1 is an HPLC elution profile of the RW1-5B fraction.

The present invention is generally directed to glucagon antagonists, as well as the production and administration thereof. As mentioned above, glucagon antagonists of this invention inhibit the stimulation of a glucagon-induced response pathway, and may be used within therapeutic compositions to treat disease states associated with elevated glucose levels, including (but not limited to) diabetes and hyperglycemia.

As used herein, the term "glucagon antagonist" means a compound that inhibits a glucagon-induced stimulation of a response pathway. A "response pathway" is a biochemical pathway activated in response to external stimuli that is generally, but not always, directly coupled to a membrane-bound receptor. Response pathways generally induce cellular responses such as extracellular matrix secretion from responsive cell lines, hormone secretion, chemotaxis, differentiation, or the inhibition of cell division of responsive cells. One such response pathway is the adenylate cyclase response pathway, which is coupled to the membrane-bound glucagon receptor. The adenylate cyclase response pathway is induced upon binding of glucagon to its cellular receptor, thereby producing increased intracellular concentrations of cAMP. This, in turn, leads to an increase in gluconeogenesis and glycogenolysis, and the accompanying release of glucose. An additional response pathway is the inositol phosphate response pathway.

In a preferred embodiment of this invention, the glucagon antagonist is skyrin, as represented by Formula (I):

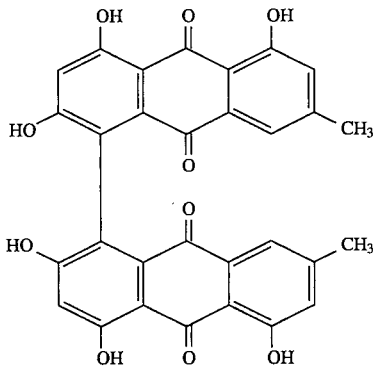

(I)

Skyrin is an orange pigment that has been isolated from both lichens (including species from the genus Lasallia and *Trypetheliopsis boninensis*) and fungi (including *Penicillium islandicum, Penicillium rugulosum, Endothia parasitica, Dermacybe austroveneta,* and *Hypomyces lactiflorum*). Skyrin has been reviewed by Ueno, *Mycotoxins—Production, Isolation, Separation and Purification*, Betina (ed.), Elsevier Science Publishers, Amsterdam, Netherlands, 1984. In addition to being an orange pigment, skyrin has been shown to uncouple oxidative phosphorylation in rat liver and rat leukemia cell mitochondria by Betinn and Kuzela (*Chem.-Biol. Interactions* 62:179–189, 1987) and Kawai et al. (*Toxic. Lett.* 20:155–160, 1984), and has been shown to selectively inhibit rice dwarf virus-RNA transcriptase by Yangai et al. (*J. Pesticide Sci*, 1:107–114, 1976). Skyrin has also been found to be non-mutagenic by Stark et al. (*J. Environ. Path. Toxic* 2:313–324, 1978). However, a number of compounds structurally similar to skyrin have been shown to be mutagenic (see e.g.,Tikkanen et al., *Mutat. Res.* 116:297–304, 1983; Stark et al., ibid.).

In addition to skyrin, glucagon antagonists of the present invention also include skyrin analogs. The skyrin analogs disclosed herein may be screened for activity as glucagon antagonists by the assays described in greater detail below. As used herein, the term "skyrin analog" means a compound represented by Formula (II):

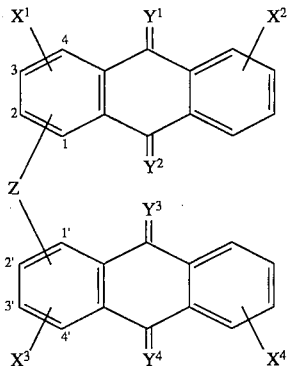

(II)

wherein:

$X^1$, $X^2$, $X^3$ and $X^4$ are, independently, one or more (i.e., at least one) of the following: hydrogen, hydroxy, alkyl, alkoxy, halogen, amino, nitro, cyano, sulfhydryl, thioalkyl, trifluoromethyl, —O-acyl or —N($R^1$)$R^2$, where $R^1$ and $R^2$ are, independently, hydrogen or alkyl;

$Y^1$, $Y^2$, $Y^3$ and $Y^4$ are, independently, one or more of the following: oxygen, sulfur or $CH_2$; and Z is an optional linker moiety and represents, alkyl, —O—, —C(=O)—, —O—C(=O)—, —S—, —C(=O)NH—, alkyl-ketone, alkyl-ether or alkyl-ester linkages.

As used herein, the term "alkyl" means a branched or unbranched, saturated or unsaturated, $C_{1-6}$ hydrocarbon chain, and includes (but is not limited to) methyl, ethyl, propyl, isopropyl, butyl, isobutyl, t-butyl, pentyl and hexyl; the term "alkoxy" means a branched or unbranched, saturated or unsaturated, $C_{1-6}$ hydrocarbon chain containing one or more oxygens, including (but not limited to) —$CH_2OH$ and —$OCH_3$; the term "halogen" means F, Cl, Br and I; and the term "—O-acyl" means a chemical moiety having the structure —O—C(=O)—$R^3$ or —O—C(=O)—NH—$R^4$, where $R^3$ is hydrogen, alkyl or an amino acid having the structure —CH($NH_2$)$R^5$, and $R^4$ is hydrogen, alkyl or an amino acid having the structure —CH(COOH)$R^5$, where $R^5$ is an amino acid side chain.

With respect to the optional Z linker moiety, the terms "alkyl-ketone", "alkyl-ether" and "alkyl-ester" means an alkyl moiety which contains a ketone, ether or ester moiety, including (but not limited to) —O—$CH_2$—, —$CH_2$—O—$CH_2$— and —$CH_2$—C(=O)O—$CH_2$—. In addition, the covalent bond between the two ring structures, with or without the optional Z linker moiety, may be between any one of the 1 through 4 carbon atoms and any one of the 1' through 4' carbon atoms (such as the 1,3' —C—C— linkage of isoskyrin), and is preferably between the 1 carbon atom and the 1' carbon atom (such as the 1,1' —C—C— linkage of skyrin).

In a preferred embodiment, the skyrin analogs of the present invention are represented by Formula (III):

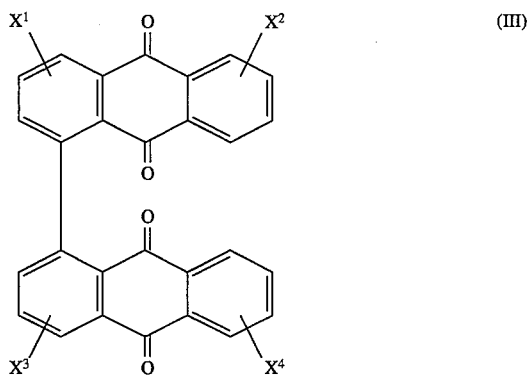

wherein $X^1$, $X^2$, $X^3$ and $X^4$ are as identified above with respect to Formula (II). The skyrin analogs of this invention, including the preferred skyrin analogs of Formula (III), may be screened for glucagon antagonist activity by the assays described in greater detail below.

In a more preferred embodiment, the skyrin analog of the present invention is oxyskyrine as represented by Formula (IV):

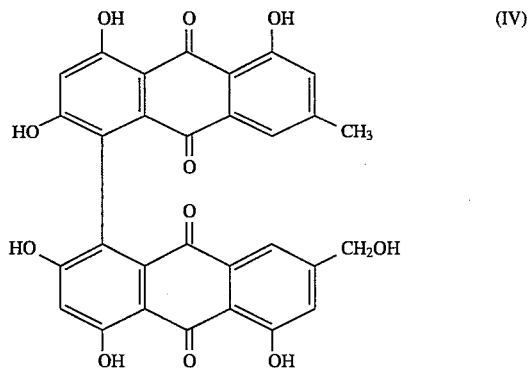

As mentioned above, skyrin has been previously isolated from both lichens and fungi. In the practice of the present invention, skyrin may be isolated from a fungal broth (as disclosed in Example 2). Alternatively, skyrin, as well as skyrin analogs, may be synthesized using know organic synthesis techniques (as disclosed in greater detail below).

With respect to the chemical synthesis of skyrin and skyrin analogs, it should be noted that skyrin belongs to a class of compounds generally known as bisanthroquinones. Bisanthroquinones can be obtained from bianthrones by oxidation, and bianthrones may be prepared by oxidative coupling of anthrones. The oxidation of anthrones and bianthrones has been extensively investigated in relation to dyestuff chemistry (see Attree and Perkin, *J. Chem. Soc*, 144, 1931). A two-step oxidative synthesis of skyrin has been described by Cameron et al. (*Aust. J. Chem.* 29:1535–1548, 1976). Treatment of emodin anthrone with ferric chloride (Adams and Jacobsen, *J. Amer. Chem. Soc.* 46:1312, 1924) produced emodin bianthrone as a pair of diastereomers (Banks et al., *Aust. J. Chem.* 29:1509, 1976). Separation by silica gel chromatography provided an equal quantity of the meso- and (+/−)-diastereomers. Oxidation of the (+/−)-diastereomer in basic acetone gave skyrin in 35% yield.

The relative ease of oxidative coupling of emodin anthrone to emodin bianthrone results from the free phenolic hydroxy groups. Less reactive, non-hydroxylated anthrones may be condensed under more severe conditions, as described by Cameron and Schutz (*J.Chem.Soc: C*:2121, 1967). A biomimetic synthesis of skyrin has also been reported by Radtke et al. (*Angew. Chem. Int. Ed, Engl,* 14:819–820, 1975). Oxidation of emodin anthrone with potassium ferrocyanide in aqueous base produced skyrin in 1.2% yield.

In the practice of the present invention, two techniques for the synthesis of skyrin analogs are preferred: (1) new anthrones may be oxidized to bianthrones by the above procedures, or (2) existing bianthrones or bisanthroquinones may be further modified to yield new skyrin analogs. In the first method, the preparation of emodin-like anthroquinones may be accomplished by the techniques disclosed above (see e.g., Attree and Perkin, supra). For example, oxygen alkylated and carbon substituted derivatives may be synthesized to provide a wide variety of functionalized anthrones and/or anthroquinones. These functionalized compounds may then be coupled and oxidized to yield skyrin analogs (see, Cameron et al., supra). The coupling of identical anthrones and subsequent oxidation produce symmetrical bisanthroquinones (e.g., skyrin), while the coupling of two different anthrones followed by oxidation provide asymmetric bisanthroquinones (e.g., oxyskyrine). Furthermore, the intermediate anthrones disclosed above need not be restricted to highly oxygenated species. For example, coupling of non-oxygenated anthrones may be facilitated under more severe reaction conditions (see Cameron and Schutz, supra). Thus, one skilled in this art will appreciate that the preparative methods disclosed herein provide a multitude of skyrin analogs.

Alternatively, existing bisanthroquinones, or those synthesized by the above methods, may be further substituted to produce skyrin analogs. For example, bianthrones which possess functional groups (such as phenolic hydroxyl groups or electrophilic carbons) may be made using known organic synthesis techniques. Moreover, the hydroxyl groups may be alkylated or acylated with a variety of reagents, and activated aromatic carbons may be sites for electrophilic substitution. In either approach, bisanthroquinones may be chemically modified by substituents to yield the skyrin analogs of the present invention. Furthermore, the substituents may be selected to effect characteristics such as solubility, as well as biological activity. For example, in Formulas (II) and (III) above, $X^1$, $X^2$, $X^3$ and $X^4$ include the —O-acyl moieties —O—C(=O)—$R^3$ and —O—C(=O)—NH—$R^4$, where $R^3$ is hydrogen, alkyl or an amino acid having the structure —CH(NH$_2$)$R^5$, and $R^4$ is hydrogen, alkyl or an amino acid having the structure —CH(COOH)$R^5$, where $R^5$ is an amino acid side chain. Thus, amino acid subsituents may be added to the skyrin analog to impart desired solubility characteristics thereto. For example, one or more lysine moieties may be added to increase water solubility, wherein such lysine moieties have the structure —O—C(=O)—CH(NH$_2$)—(CH$_2$)$_4$NH$_3$ or —O—C(=O)—NH—CH(COOH)—(CH$_2$)$_4$NH$_3$.

In a further embodiment of the present invention, the linkage between the two anthroquinone halves of the skyrin analog (for example, the 1,1' —C—C— bond) may be optionally modified by the addition of one or more atoms or chemical moieties. Specifically, such linkage modifications include alkyl, —O—, —C(=O)—, —O—C(=O)—, —S—, —C(=O)NH—, alkyl-ketone, alkyl-ester and alkyl-ether moieties. Synthesis of such skyrin analogs may involve the preparation of anthroquinones with appropriate functionality at the 1-position. For example, an anthroquinone with a carboxylic acid group at position 1 may be condensed with another anthroquinone with a primary alcohol at position 1' to yield an ester-linked bisanthroquinone. A carboxylated anthroquinone may also be condensed with one bearing a primary amine at position 1 to produce an amide-linked bisanthroquinone. Similar linkages may be made between carbon atoms other than the 1,1' —C—C— linkage, such as the 1,3' —C—C— linkage. One skilled in the art may generate the linkage moieties of this invention using known organic synthesis techniques (see, e.g., Pal and Pal, *J. Indian Chem. Soc.* 66:236–238, 1989).

As mentioned above, the preferred compounds of the present invention— that is, skyrin and skyrin analogs— function as glucagon antagonists. In general, glucagon antagonists may be identified by their ability to inhibit or reduce stimulation of cAMP production, relative to the cAMP production in the presence of native glucagon alone, as determined in an adenylate cyclase assay. Adenylate cyclase assays are described, for example, by Lin et al. (*Biochemistry* 14:1559–1563, 1975; which is incorporated herein by reference in its entirety). Biological responses via the inositol triphosphate pathway may be assessed by measuring inositol phosphate metabolism as generally described in Subers and Nathanson (*J. Mol. Cell. Cardiol*, :131–140, 1988; which is incorporated herein by reference in its entirety) or Pittner and Fain (ibid,; which is incorporated herein by reference in its entirety) or by measuring the intracellular calcium concentration as generally described by Grynkiewicz et al. (*J. Biol. Chem*, 260:3440–3450, 1985; which is incorporated herein by reference in its entirety).

In a preferred embodiment, glucagon antagonists, including the skyrin analogs of the present invention, are identified through their ability to specifically inhibit the glucagon-induced adenylate cyclase response pathway. Glucagon receptors have been reported in a number of tissues, for example, liver, kidney, cardiac muscle and adipose tissue from a number of species including dog, pig, human and rat. In addition, host cells expressing recombinant glucagon receptors may also be used. Recombinant glucagon receptors and host cells transformed with recombinant glucagon receptors have been described by Kindsvogel et al. PCT Publication No. WO 94/05789, which is incorporated herein by reference in its entirety). Adenylate cyclase activity assays may be carried out using, for example, the method described by Lin et al. (*Biochemistry* 14:1559–1563, 1975). These methods measure the level of stimulation of cAMP production relative to native glucagon and generally involve exposing a membrane preparation from tissue containing glucagon receptors to a mixture of glucagon and the glucagon antagonist in the presence of ATP. Membrane preparations from rat liver are generally used for adenylate cyclase activity assays, although other tissues containing glucagon receptors or host cells expressing a recombinant glucagon receptor may be used. Membranes may be prepared using the method described by Neville (*Biochim. Biophys Acta*, 154:540–552, 1968) as modified by Pohl (*Methods in Receptor Research*, Ed. Blecher, M., New York, pp 160–164, 1976). Briefly, young female Sprague-Dawley rats are used for the preparation of the liver membranes; however, other laboratory strains are acceptable. Sixty to one hundred grams of rat liver are batch-processed by first mincing the tissue into approximately 3–6 mm pieces. The minced tissue is suspended in ice cold 1 mM sodium bicarbonate at a concentration of approximately 300 g/l. The suspension is batch-processed in a tissue homogenizer with eight strokes of the loose pestle. The homogenate is mixed with additional ice cold 1 mM sodium bicarbonate to yield a final concentration of about 40–80 g/l. The diluted homogenate is stirred for at least three minutes following which it is filtered through a double layer of cheese cloth. The filtrate is refiltered through four layers of cheese cloth, transferred to centrifuge bottles and centrifuged at 1500×g for 30 minutes at 4° C.

After centrifugation, the supernatant is carefully decanted and discarded, and the pellets are gently resuspended in the remaining supernatant with three strokes of the loose pestle in a clean tissue homogenizer. The volume of the resuspended supernatant is brought to a total of 165 ml in a final concentration of 44% sucrose. After thorough mixing, the sucrose concentration is measured with a refractometer and adjusted to between 43.9% to 44.1% sucrose (corresponding to a refractive index between 1.4076 and 1.4080) with either 69% sucrose or water. The adjusted suspension is distributed into six 1"×3.5" cellulose nitrate tubes, and the tubes are filled and balanced by overlaying with a fresh sucrose solution which has been adjusted to a concentration between 42.2% to 42.4% sucrose (corresponding to a refractive index between 1.4042 and 1.4046). The samples are centrifuged in a swinging bucket ultracentrifuge rotor appropriate to the tubes being used (e.g., Beckman SW28 or SW25.2; Beckman Instruments, Inc., Fullerton, Calif.), at 25,000 rpm for 150 minutes at 4° C. (i.e., 100,000–150,000 G).

The purified membranes are recovered as a layer floating at the top meniscus of the tubes by either scooping with a spoon-shaped spatula or removal by suction into a syringe through an 18-gauge needle. The membranes are resuspended in 10 ml of 1 mM bicarbonate by suction and expulsion from a 10–25 ml syringe through an 18-gauge or 20-gauge needle. Following resuspension, the membranes are washed by adding 60–80 ml of 1 mM bicarbonate and centrifugation at 15,000 rpm (i.e., 26890 G) in a high speed centrifuge. The supernatants are discarded, and the pellets are resuspended in 1 mM bicarbonate and pooled to yield approximately 5–10 ml of concentrated hepatocyte membranes. The membrane preparation is aliquoted and stored frozen at −80° C. for up to six months.

The protein concentration of the membrane preparation is determined by diluting 10–20 µl of the membrane preparation 100-fold in 1M NaCl, 0.17M sodium phosphate (pH 7.0) buffer. The absorbance of this solution relative to the buffer is measured in 1-cm quartz cuvettes at 224 nm and 236.5 nm wave length in a UV spectrophotometer. Protein concentration is calculated according to the formula:

$$A_{224nm} - A_{236.5nm} = (\text{mg/ml protein})(6.45)(100)$$

An adenylate cyclase activity assay is carried out by first preparing Solution A, Solution B, 100× glucagon stock, and Stop Mix. Solution A contains between 50 mM and 200 mM Tris HCl at between pH 7.4 to 7.8, between 20 mM to 100 mM $MgCl_2$, and between 0.2% to 0.4% bovine serum albumin (BSA). It may be preferable to add between 2 and 8 mg/ml of creatine phosphokinase (Sigma Chemical Co., St. Louis, Mo.). Most preferably, Solution A contains 100 mM Tris HCl pH 7.6, 20 mM $MgCl_2$, 0.4% BSA, 4 mg/ml creatine phosphokinase. Solution B contains between 0.4 and 20 mM ATP, between 1.6 µM and 25 mM GTP, between 0 and 4 mM isobutyl-1-methyl-xanthine (IBMX) and between 2 and 8 mM EDTA. It may be preferable to add between 60 mM and 240 mM creatine phosphate (Sigma Chemical Co.). Most preferably, Solution B contains 4 mM ATP, 20µM GTP, 4 mM IBMX, 4 mM EDTA, and 120 nM creatine phosphate. 100× glucagon solution contains 1µM glucagon. Stop mix contains 100 mM acetic acid, 50 mM EDTA. Alternatively, the reactions may be stopped by heating the reaction in a boiling water bath for 5 minutes.

The adenylate cyclase reaction, which converts ATP to cAMP, may be carried out by adding the glucagon antagonist to the wells of a microtiter plate at micromolar concentrations. Equal volumes of Solution A and Solution B are mixed, and 50 µl of the mixture is added to each negative control well. Glucagon is added to the remaining Solution A+Solution B mixture to a final concentration of $1\times10^{-8}$M from the 100×glucagon stock solution, and 50 µl of this solution is added to each well containing the glucagon antagonist. The membrane preparation is diluted with water to between 0.2 and 10 mg/ml, preferably 2 mg/ml protein, and 45 µl of the diluted membranes is added to each well to start the reaction. The reaction mixtures are incubated at room temperature for 12 minutes, and the reactions are stopped by the addition of 100 µl of Stop solution to each well. The reactions are clarified by centrifugation and stored at 4° C.

In general, cAMP production is measured by the conversion of $^{32}$P-ATP to cAMP. Cyclic AMP production may be measured using the method of Salomon et al. (*Anal, Biochem,* 58:541–548, 1976) or Krishna et al. (*J. Pharmacol. Exp. Ther.* 163:379, 1968), or may be measured using a commercially available kit. However, it is preferred that cAMP production be measured using a Scintillation Proximity Assay kit manufactured by Amersham (Arlington Heights, Ill.). Using the manufacturer's directions, the Amersham Scintillation Proximity Assay Kit is used to measure the production of cAMP by competition of iodinated-cAMP with anti-cAMP antibodies. Preferably, 10 µl of each adenylate cyclase reaction is added to individual beta plate wells, and each reaction is diluted with 65 µl of NaAcetate. Standards are prepared at 1.6 pMole and 6.4 pMole from the non-acetylation standards supplied with the Amersham kit, and 75 µl of each standard is added to triplicate sample wells. One hundred-fifty microliters of buffer (Amersham) is added to triplicate wells for nonspecific binding controls. Seventy-five microliters of $^{125}$I-cAMP is added to each well. Seventy-five microliters of diluted rabbit anti-succinyl cAMP is added to each well, except the nonspecific binding control wells. Seventy-five microliters of diluted anti-rabbit SPA reagent is added to each well, and the plates are sealed and incubated overnight at room temperature with shaking. After the overnight incubation, the reactions are counted in a beta-plate counter (Pharmacia, Uppsala, Sweden).

Within this embodiment, glucagon antagonists (including skyrin analogs as described herein) may be identified as those which inhibit the stimulation of the rat liver membrane adenylate cyclase by glucagon. The percent response may be determined using the formula:

$$\%R_x = (CPM - CPM_{NSB})/(CPM_{0.0} - CPM_{NSB})$$

where $\%R_x$=Percent response for a given sample or standard

CPM=Sample counts $CPM_{NSB}$=Mean NSB control counts $CPM_{0.0}$=Mean 0.0M standard counts The relative concentration of cAMP for a given sample may be determined using the formula:

$$[cAMP]_x = 1.6 eln4(\%R_x - \%R_{1.6})/(\%R_{6.4} - \%R_{1.6})$$

where $[cAMP]_x$=the relative concentration of a given sample $\%R_x$=Percent response for a given sample $\%R_{1.6}$=Percent response for the $1.6\times10^{-9}$M standard $\%R_{6.4}$=Percent response for a the $6.4\times10^{-9}$M standard Thus, assay wells containing significantly less cAMP than the average may be identified as containing glucagon antagonists.

The glucagon antagonists of the present invention, including skyrin and skyrin analogs, may be used therapeutically. In general, the glucagon antagonist may be administered by, for example, parenteral administration or by infusion of a pharmaceutical composition containing the glucagon antagonist, as well as by oral administration of the glucagon antagonist in combination with an acceptable carrier. Pharmaceutical compositions of this invention include the glucagon antagonist in combination with one or more pharmaceutically acceptable carriers and/or diluents. Suitable carriers and diluents include, but are not limited to, aqueous isotonic solutions, and may further include sodium chloride, dextrose, boric acid, sodium tartrate, and propylene glycol. In addition, suitable salts of skyrin or skyrin analogs may also be employed. Solubility of skyrin and skyrin analogs may be adjusted by appropriated chemical modification to the compound, or by appropriate choice of suitable pH buffers. Alternatively, the skyrin or skyrin analogs of this invention may be emulsified with suitable agents to aid in administration of the compounds. Therapeutic doses of glucagon antagonists of the present invention may be between 10 µM and 100 µM, and may be administered simultaneously with other compounds, such as insulin, either in the same composition or in separate compositions. One skilled in this art may formulate the compounds of the present invention in an appropriate manner, and in accordance with accepted practices, such as those disclosed in *Remington's Pharmaceutical Sciences,* Gennaro, Ed., Mack Publishing Co., Easton, Pa., 1990 (which is incorporated herein by reference in its entirety).

The following examples are provided for purposes of illustration, not by way of limitation.

EXAMPLES

The various mediums referenced in the following examples are identified below in Table 1.

TABLE 1

| ZG-A Medium: | |
|---|---|
| 5.0g. | Glucose (Mallinckrodt Inc.) |
| 40.0 g | Lactose (Land O'Lakes) |
| 30.0 g | Pharmamedia (Traders Protein) |
| 5.0 g | Peptone (Difco) |
| 0.5 g | KH$_2$PO$_4$ (Mallinckrodt Inc.) |
| 0.5 g | MgSO$_4$.7H$_2$O (Sigma Chem. Co.) |
| 0.3 g | KCl (Sigma Chem. Co.) |
| 3.0 g | CaCO$_3$ (Sigma Chem. Co.) | dissolve solids in water and bring to a final volume of 1 liter, adjust the pH to 7.0, aliquot 30 ml into 250 ml flask and autoclave 15 minutes

| ZG-B Medium: | |
|---|---|
| 10.0g. | Glucose (Mallinckrodt Inc.) |
| 30.0 g | Hayashi starch (Hayashi Hanawa, Osaka, Japan) |
| 5.0 g | Casamino acids (Difco Laboratories Inc., Detroit, MI) |
| 3.0 g | Beef extract (Difco Laboratories Inc.) |
| 2.0 g | Yeast extract (Difco Laboratories Inc.) |
| 3.0 g | N-Z Amine (ICN Biochemicals, Cleveland, OH) |
| 0.5 g | K$_2$HPO$_4$ (Mallinckrodt Inc.) |
| 0.5 g | MgSO$_4$.7H$_2$O (Sigma Chemical Co.) |
| 0.3 g | KCl (Sigma Chemical Co.) |
| 3.0 g | CaCO$_3$ (Sigma Chemical Co.) | dissolve solids with water and bring to a final volume of 1 liter, adjust the pH to 7.0, aliquot 30 ml into 250 ml flask and autoclave 15 minutes

| ZG-C Medium: | |
|---|---|
| 20.0 g | Glycerol (Sigma Chem. Co.) |
| 20.0 g | Dextrin (Sigma Chem. Co.) |
| 10.0 g | Soytone (Difco) |

TABLE 1-continued

| | |
|---|---|
| 3.0 | g Yeast Extract (Difco) |
| 2.0 | g (NH$_4$)$_2$SO$_4$ (Mallinckrodt Inc.) |
| 2.0 | g CaCO$_3$ (Sigma) | dissolve solids in water and bring to a final volume of 1 liter, adjust the pH to 7.0, aliquot 30 ml into 250 ml flask and autoclave 15 minutes

ZG-D Medium:

| | |
|---|---|
| 30.0 | g Glycerol (Sigma Chem. Co.) |
| 30.0 | g Beef extract (Difco) |
| 1.0 | g Tryptophan (Sigma Chem. Co.) |
| 0.5 | g KH$_2$PO$_4$ (Mallinckrodt Inc.) |
| 0.5 | g MgSO$_4$.7H$_2$O (Sigma Chem. Co.) |
| 0.3 | g KCl (Sigma Chem. Co.) |
| 3.0 | g CaCO$_3$ (Sigma Chem. Co.) | dissolve solids in water and bring to a final volume of 1 liter, adjust the pH to 7.0, aliquot 30 ml into 250 ml flask and autoclave 15 minutes

ZG-S Medium:

| | |
|---|---|
| 20.0 | g Glucose (Mallinckrodt Inc., St. Louis, MO) |
| 15.0 | g Pharmamedia (Traders Protein, Memphis, TN) |
| 3.0 | g (NH$_4$)$_2$SO$_4$ (Mallinckrodt Inc.) |
| 0.03 | g ZnSO$_4$.7H$_2$O (Sigma Chem. Co., St. Louis, MO) |
| 4.0 | g CaCO$_3$ (Sigma Chem. Co.) | dissolve the solids in water and bring the final volume to 1 liter, aliquot 25 ml into 250 ml flask and autoclave 15 minutes

LCSB Agar:

| | |
|---|---|
| 1.5% | Lactose (Land O'Lakes) |
| 0.5% | Corn steep liquor (Sigma Chemical Co.) |
| 0.5% | Peptone (Difco) |
| 0.4% | NaCl (Sigma Chem. Co.) |
| 0.05% | MgSO$_4$.7H$_2$O (Sigma Chem. Co.) |
| 0.06% | KH$_2$PO$_4$ (Mallinckrodt Inc.) |
| 0.0005% | FeCl$_3$.H$_2$O |
| 0.0002% | CuSo$_4$.H$_2$O |
| 3.0% | Agar | adjust pH to 4.8, autoclave and pour plates

Example 1

Screening of Fungal Broth

The glucagon antagonists of this invention were identified by screening numerous fungal broths, plant extracts, and marine organism extracts. This example describes the initial screening of the fungal broth for glucagon antagonists, and the subsequent isolation of the Z-522 isolate.

Isolated fungal or actinomycete cultures were plated on LCSB agar (Table 1) containing 20 µg/ml tetracycline and 130 µg/ml deoxycholate. The samples were incubated at 27° C. for seven days. Seed cultures were prepared by inoculating isolated colonies into 30 ml of ZG-S medium (Table 1). The cultures were incubated in a shaker giving a 3-inch throw at 220 rpm at 28° C. for 48 hours. A two-milliliter aliquot of seed culture was then added to each of the four different fermentation medium: ZG-A, ZG-B, ZG-C and ZG-D (Table 1). The cultures were next incubated as described above for 96 hours. After 96 hours, a four-milliliter aliquot of each culture was removed to a test tube and extracted with 4 ml of ethyl acetate by vortexing the samples vigorously for 2–3 minutes with subsequent centrifugation to separate the phases. A two-milliliter aliquot of each sample was removed from the upper phase to a fresh tube, and the sample was dried on a speed-vac. The dried extracts were resuspended in 200 µl of DMSO (the resuspended extracts represented a 10× broth concentration). The extracts were each diluted 1:5 in DMSO, and 5 µl of the dilution was assayed for glucagon antagonist activity (Example 4). One isolate, Z-522, showed glucagon antagonist activity.

This specific isolate (Z-522) was isolated from soil collected in Sumner County, Ks. The soil was air dried at less than 40° C. and was plated on LCSB agar (Table 1) containing 20 µg/ml tetracycline and 130 µg/ml deoxycholate. The sample was incubated at 27° C. for seven days. Colony isolates were obtained and subsequently plated on LCSB agar (Table 1) containing 130 µg/ml deoxycholate. The plates were grown at 28° C. for seven days. Isolated colonies were 10 mm to 20 mm in diameter. Each colony had a flat outer edge containing blue-green spores and round conidia. The center of each colony had raised white to colorless mycelia with droplets on the aerial mycelia and blue-green to olive green conidia that were elongated and more tufted or brush-like.

Example 2

Purification of Glucagon Antagonist from the Z-522 Isolate

One hundred seed cultures of Z-522 isolate were prepared by inoculating Z-522 into 25 ml of ZG-S medium (see Table 1) and incubating the cultures in a shaker giving a 3-inch throw at 220 rpm at 28° C. for 48 hours. A two-milliliter aliquot of each seed culture was used to inoculate one of 100 flasks containing 30 ml of ZG-B medium (see Table 1). The cultures were grown in shakers as described above for an additional 96 hours. At the end of the 96-hour fermentation, a 4-ml aliquot of each culture was removed into a test tube. The cultures were each extracted with 4 ml of ethyl acetate by vortexing each test tube vigorously for 2–3 minutes followed by centrifugation at 3500 rpm for 15 minutes. A 2-ml aliquot of the organic (upper) phase from each tube was removed and pooled. The pooled extracts were evaporated to dryness. The 2938 mg of the crude ethyl acetate extract was distributed into 88 vials, each of which contained 33.4 mg of crude extract.

The contents of 84 vials were dissolved in a total of 270 ml of methanol, and the dissolved material was combined into a 1000 ml separatory funnel. The volume in the separatory funnel was brought to 300 ml by the addition of 30 ml of water such that the final solution contained 90% methanol and 10% water. The methanol/water solution was extracted with 150 ml of hexane. The funnel was vigorously shaken for one minute, and the layers were allowed to separate. The lower, aqueous layer was drawn off into another 1000 ml separatory funnel, and the hexane layer was drawn into a 1000 ml round-bottom flask. The hexane extraction was repeated two more times, and the hexane layers were combined in the round-bottom flask. The volume of the methanol/water solution was increased to 385.7 ml by the addition of 85.7 ml of water to bring the final solution to 70% methanol and 30% water. The methanol/water solution was extracted with 200 ml of chloroform. As in the extractions described above, the flask was shaken vigorously for one minute, and the layers were allowed to separate. The lower, chloroform layer was drawn off into a 1000 ml round-bottom flask. The methanol/water solution was re-extracted two more times with chloroform, and the chloroform layers were combined into the 2000 ml round-bottom flask. The chloroform fraction was evaporated on a rolo-evaporator. The residue from the chloroform fraction, designated RW1-5B, weighed 1.9468 g.

A 200 mg portion of the dried RW1-5B fraction was dissolved in 1 ml of acetone. To this solution, 4 ml of hexane was added. A 2×23 cm column of silica gel (Baker) was slurry-packed in 60:40 hexane:acetone. The RW1-5B slurry was delivered to the top of the column, and the material was eluted with 60:40 hexane:acetone under slight nitrogen pressure. Eluant fractions of 10 ml each were collected, and skyrin eluted as a bright orange band. Fractions were tested for purity by analytical HPLC using reverse phase chromatography (Rainin C-18, 5 mm, 4.6×150 mm) using a gradient elution of 30% acetonitrile (with 0.05% trifluoroacetic acid (TFA))/70% water (with 0.05% TFA) to 100% acetonitrile (with 0.05% TFA) over 35 minutes, with the final percentage held for ten minutes at a flow rate of 1.0 ml/min and using a diode-array-detector with pilot signal at 45 nm. Only fractions that were pure by analytical HPLC were combined to give 17.6 mg of skyrin.

In an alternative method, skyrin was purified by first dissolving 200 mg of RW1-5B into 4 ml of a 1:1 chloroform:methanol solution. The solution was filtered through a 0.45 µm filter, and 1 ml of this solution was injected into a reverse phase preparative column (Beckman C-18, 10 1, 21.4×150 mm) using a gradient elution of 25% acetonitrile (with 0.05% TFA)/75% water (with 0.05% TFA) to 100% acetonitrile (with 0.05% TFA) over 60 minutes at a flow rate of 20 ml/min and with detection between 270 and 380 nm. This chromatography was carried out on a Gilson HPLC system with a model 306 pump and a model 116 variable wave length detector. Fractions were collected every 30 seconds into 12× 150 mm tubes. Fractions were assayed for biological activity as described below. Two areas of biological activity were identified corresponding to oxyskyrine and skyrin, which eluted at 20 minutes (fraction 43) and 32 minutes (fraction 55), respectively (see FIG. 1). Using the preparative chromatography method, 0.5 mg of oxyskyrine and 14.5 mg of skyrin were recovered.

Example 3

Identification of Glucagon Antagonists

Figure 2:
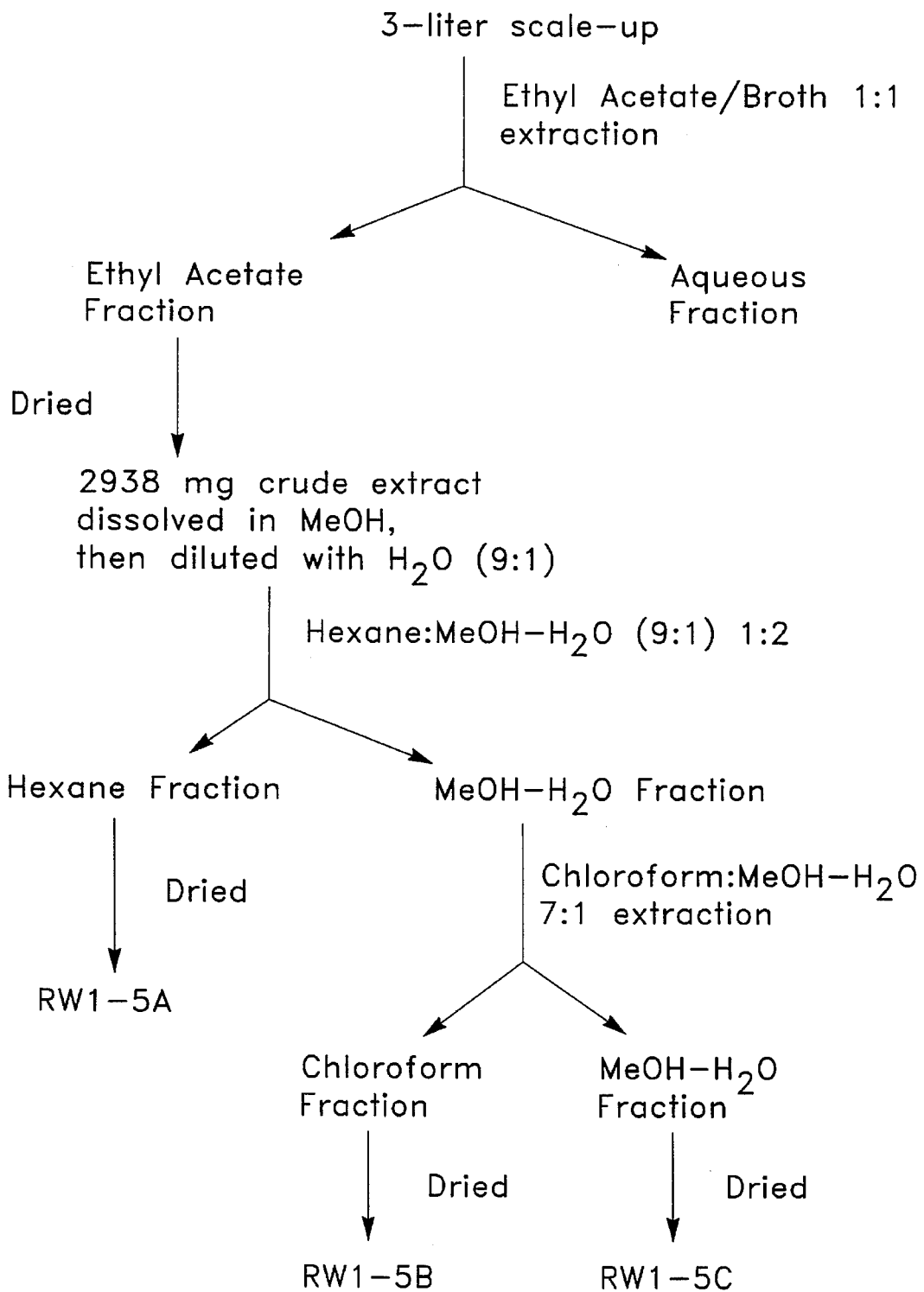
FIG. 2 is a flow diagram of the purification of the Z-522 isolate.

FIG. 2 illustrates the purification of the Z-522 isolate as disclosed in Example 2 above. Fraction RW1-5B was subjected to HPLC, and the HPLC fractions were assayed for glucagon receptor-specific adenylate cyclase inhibition as disclosed in Example 4 below. Two fractions from each of the highest glucagon antagonist activity peaks (i.e., fractions 43 and 55) were subjected to U.V. analysis and chromatography. While the U.V. spectra of the samples were identical, HPLC revealed that the samples were different compounds.

The material in fraction 55 was subjected to fast atom bombardment high resolution mass spectrometry (VG Analytical, Manchester, England), giving an $(M+H)^+$ of 539.0954, which demanded a molecular formula, $M+H^+$, of $C_{30}H_{19}O_{10}$ (calculated at 539.0978). $^1$H-NMR and $^{13}$C-NMR were then conducted on this compound on a 300 MHz Bruker AF300 NMR (Bruker Analytische Messtechnik GMBI, Karlsruhe, Germany). The presence of three aromatic singlets and a single aryl-methyl group was shown by $^1$H-NMR. The $^{13}$C-NMR revealed the presence of 15 carbon signals: 1 methyl carbon, 12 aromatic carbons and 2 carbonyl carbons. The results from the $^{13}$C-NMR, coupled with the molecular formula of $C_{30}H_{18}O_{10}$, indicated that the compound was a dimer.

In a parallel procedure, the other active peak, fraction 43, was purified by preparative reverse phase HPLC chromatography and subjected to low resolution mass spectrometry. The molecular weight of the compound was 554. $^1$H-NMR and $^{13}$C-NMR of this compound indicated a doubling of the signals compared to those from fraction 55. This indicated that this compound was apparently an unsymmetrical dimer similar in structure to that found in fraction 55, with an additional 16 mass units which indicated the presence of an additional oxygen in the molecule.

The spectral data indicated that the two compounds were bisanthraquinones (based on the NMR, mass-spectral and ultraviolet data) and that fraction 55 was a symmetrical dimer with three aromatic singlet protons, and one aryl methyl group on each half of the dimer. The second compound, fraction 43, had a similar structure, but had one additional oxygen on one half of the molecule. A manual search through the Dictionary of Antibiotics and Related Substances (Bycroft (ed.)., Chapman & Hall, N.Y., 1988) showed that the compound, oxyskyrine, had the molecular formula of $C_{30}H_{18}O_{11}$ and fit the structural requirements of the first peak of activity.

A comparison of published spectral data from oxyskyrine and skyrin with the spectral data generated for fractions 43 and 55, respectively, showed that these compounds were the same. This was confirmed by a search of the modified Berdy database using $UV_{max}$ and molecular weight information, which identified skyrin as the only positive identification out of 20,000 compounds from natural product sources.

Example 4

Assay for Glucagon Antagonist Activity

Liver plasma membranes for use in adenylate cyclase assays were prepared essentially as described by Neville et al. (*Biochim. Biophys. Acta* 154:540–552, 1968) as modified by Pohl (*Methods in Receptor* Research, Blecher (ed.), New York, pp. 160–164, 1976). Twenty rats were euthanized by decapitation, and the livers were removed and cooled to 4° C. After cooling, the livers were maintained at 4° C. during the membrane preparation. The approximate volume of the livers was determined. Three volumes of medium (1 mM $NaHCO_3$, 0.5 mM $CaCl_2$) were added to the livers, and the liver tissue was roughly minced with scissors. The minced tissue was divided into two parts, and each part was homogenized for thirty seconds in a Waring-type blender at full speed. After homogenization, the homogenates were each transferred to a sieve with a 1.5 mm pore size, and the homogenates were strained through the sieve. The straining procedure was repeated for each homogenate through a finer screen. The strained homogenates were combined, and medium was added to a final volume of one liter. The homogenate was further homogenized with a Dounce homogenizer using eight vigorous strokes of the loose pestle. The homogenates were filtered through four layers of cheesecloth. The strained homogenates were centrifuged at approximately 150×g in a swinging bucket rotor for 20 minutes at 4° C. The supernalant was discarded, and the precipitate was resuspended in 500 ml of medium and homogenized in a Dounce homogenizer with three strokes of the loose pestle. The centrifugation was repeated, and the resulting precipitate was resuspended in 250 ml of medium. The homogenate was centrifuged as described, and the precipitate was suspended in 50 to 100 ml of medium. The suspension was homogenized in a Dounce homogenizer with three strokes of the loose pestle. Sucrose from a 69% sucrose solution was added to the suspension to a final sucrose concentration of 44.0±0.1%. The solution was centrifuged in an ultracentrifuge at approximately 100,000×g for 150 minutes. The membranes were removed from the top of the tube with a spoon. The membranes were stored at −80° C.

Adenylate cyclase assays were carried out in the presence and absence of 20 mM skyrin diluted in DMSO. Glucagon (Mallinkrodt Inc. St. Louis, Mo.) was dissolved in 10% acetic acid and lyophilized in 25-µg portions. The lyophilized glucagon was dissolved in 100 µl of 0.05M HCl and left for three minutes, after which the glucagon was serially diluted in buffer (2.5% human serum albumin (Grade 5, Sigma Chemical Co., St. Louis, Mo.) in 0.1M HEPES, 0.15M NaCl, pH 7.4) to final concentrations of between 0 and 100 nM. Aliquots of the membrane preparations were thawed and diluted with water to a protein concentration of approximately 3–5 mg/ml.

For each 96-well assay plate, triplicate samples were assayed in the presence and absence of 20 µM skyrin. Twenty microliters of each glucagon dilution was added to individual wells of a 96-well microtiter plate in triplicate. Five microliters of 20 µM skyrin in DMSO or 5 µl of DMSO alone was added to each well. Fifty microliters of incubation mixture (0.1% human serum albumin (Grade 5, Sigma), 15 mM $MgCl_2$, 1 mM ATP, 0.9 mM IBMX (3-isobutyl-1-methylxanthine, Sigma), 15 mM creatine phosphate, and 5 mg/ml creatine phosphokinase in 50 mM Tris-HCl (pH 7.4) was then added to each well.

The reaction was initiated by the addition of 25 µl of diluted plasma membrane prepared as described above. The plates were incubated at room temperature for 12 minutes. Following the incubation, the reaction was stopped by the addition of 100 µl of 100 mM acetic acid, 50 mM EDTA.

Figure 3:
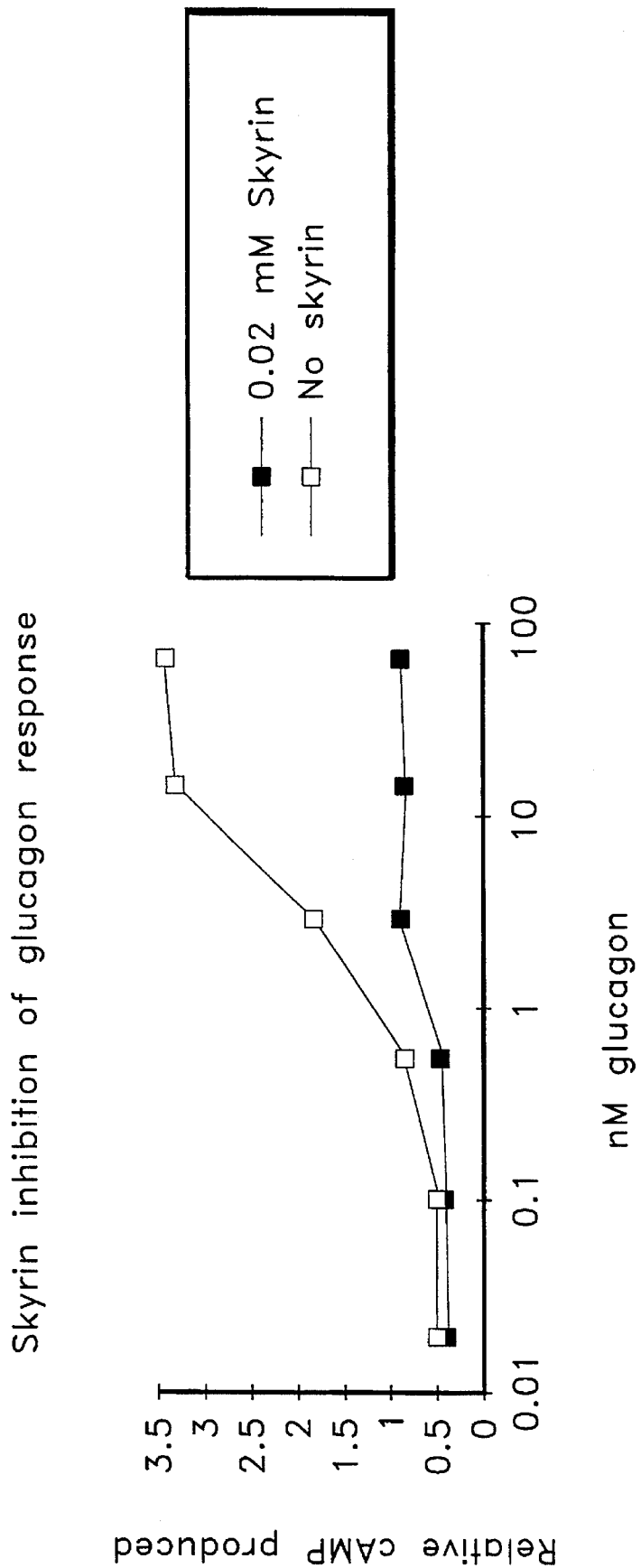
FIG. 3 illustrates the inhibitory effect of a glucagon antagonist of this invention, skyrin, on cAMP response to glucagon as measured by the Amersham Scintillation Proximity Assay kit.

The cAMP produced in each reaction was determined by assaying 10 µl of each sample using an Amersham Scintillation Proximity Assay kit (Amersham, Arlington Heights, Ill.). The results from these assays showed that skyrin inhibited the cAMP response to glucagon (FIG. 3).

Figure 4:
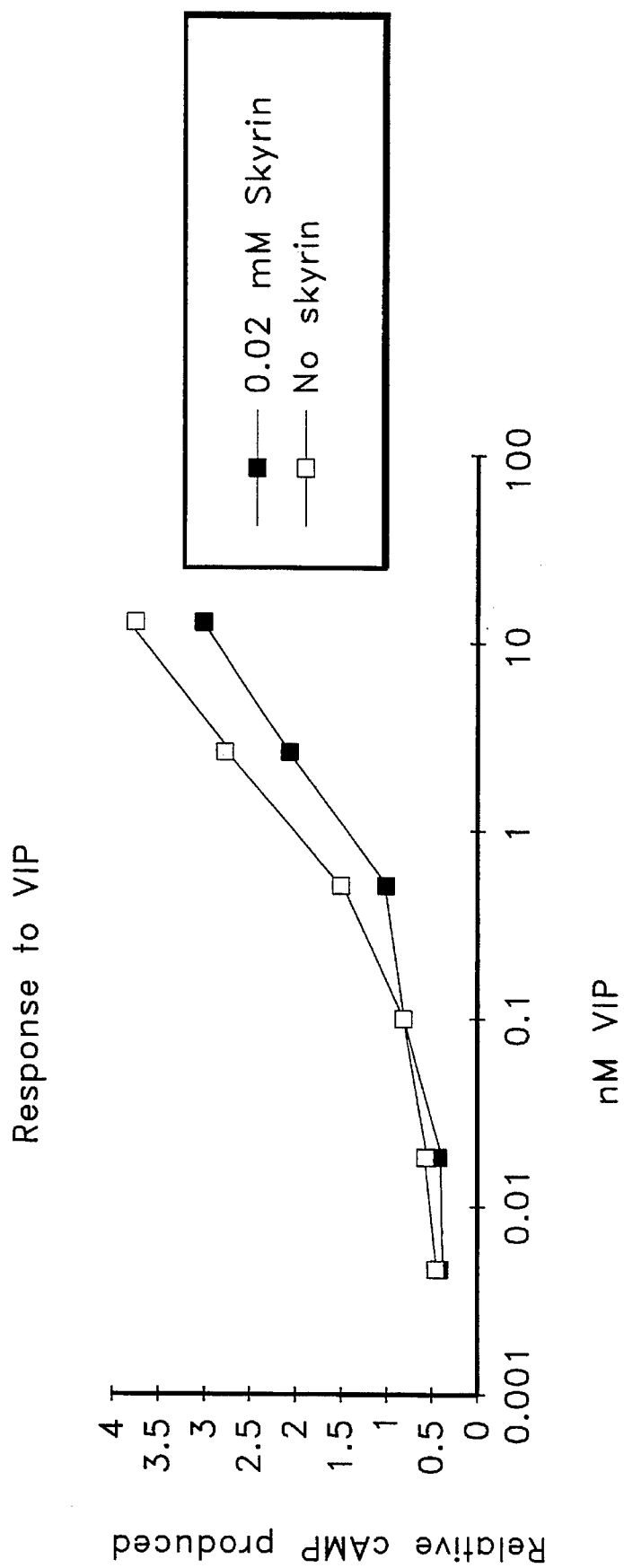
FIGS. 4 and 5 illustrate the specificity of skyrin to the glucagon receptor in assays utilizing VIP and CGRP as ligands.
Figure 5:
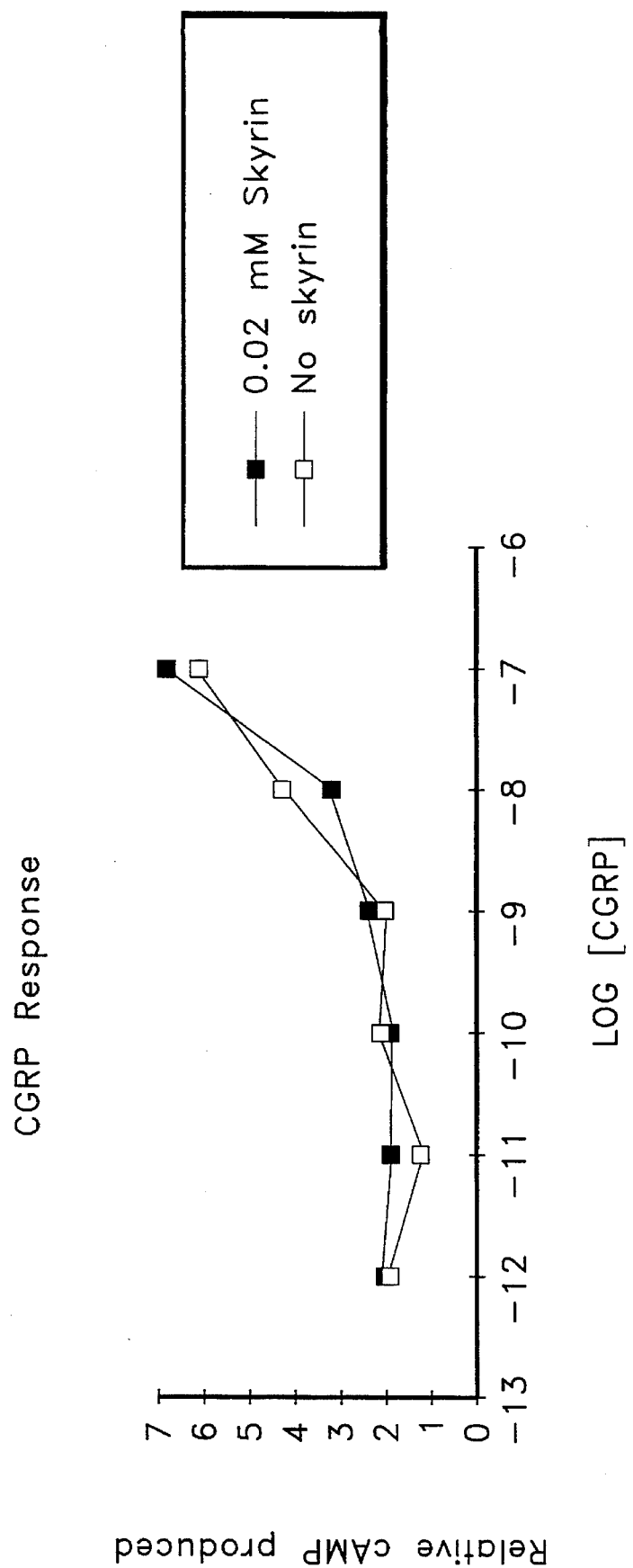
Figure 6:
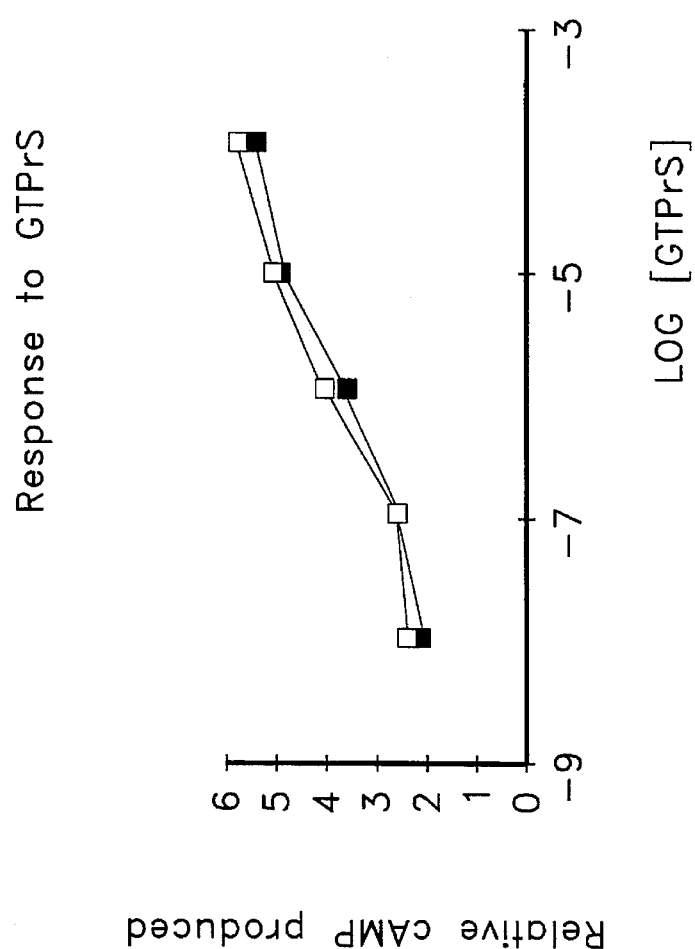
FIG. 6 illustrates that the effect of skyrin occurs at the glucagon receptor level as demonstrated by an assay utilizing GTPγS.

The specificity of the skyrin antagonist activity was assessed by replacing the serial dilutions of glucagon with serial dilutions of vasoactive intestinal peptide (VIP; Sigma Chemical Co., St. Louis, Mo.), calcitonin gene-related peptide (CGRP), forskolin (Calbiochem, San Diego, Calif.) and GTP-γS. VIP and CGRP bind to G protein-coupled receptors in liver membranes that can stimulate cAMP production. Assays using VIP and CGRP as ligands demonstrated that skyrin did not affect the stimulation of these non-glucagon G protein-coupled receptors, confirming the specificity of skyrin antagonist activity to the glucagon receptor (FIG. 4 and FIG. 5). GTPγS and forskolin, which produce receptor-independent stimulation of cAMP production, were each used to stimulate the production of cAMP in the presence and absence of 0.02 mM skyrin. Measurement of cAMP production by GTPγS or forskolin in the presence and absence of 0.02 mM skyrin showed that the cAMP levels were unaffected by skyrin, indicating that the action of the antagonist occurs at the receptor level rather than acting at a post-G protein level. FIG. 6 shows that GTPγS-stimulated cAMP levels are uneffected by the presence of 0.2 mM skyrin.

Parallel assays were prepared in the presence of serial dilutions of skyrin, oxyskyrine, a chloroform extract of the Z-522 supernatant diluted in DMSO or an ethyl acetate extraction of the Z-522 supernatant diluted in DMSO. For each assay triplicate samples were assayed. Twenty microliters of each dilution was added to individual wells of a 96-well microliter plate in triplicate. Five microliters of 5 nM glucagon (Mallinckrodt) was added to each well. Fifty microliters of incubation mixture (0.1% human serum albumin, Grade 5, Sigma), 15 mM $MgCl_2$, 1 mM ATP, 0.9 mM IBMX, 15 mM creatine phosphate, and 5 mg/ml creatine phosphokinase in 50 mM Tris-HCl (pH 7.4)) was added to each well. The reactions were initiated by the addition of 25 µl of diluted plasma membrane described above. The plates were incubated at room temperature for 12 minutes. Following incubation, the reaction was stopped by the addition of 100 µl of 100 mM acetic acid, 50 mM EDTA.

Figure 7:
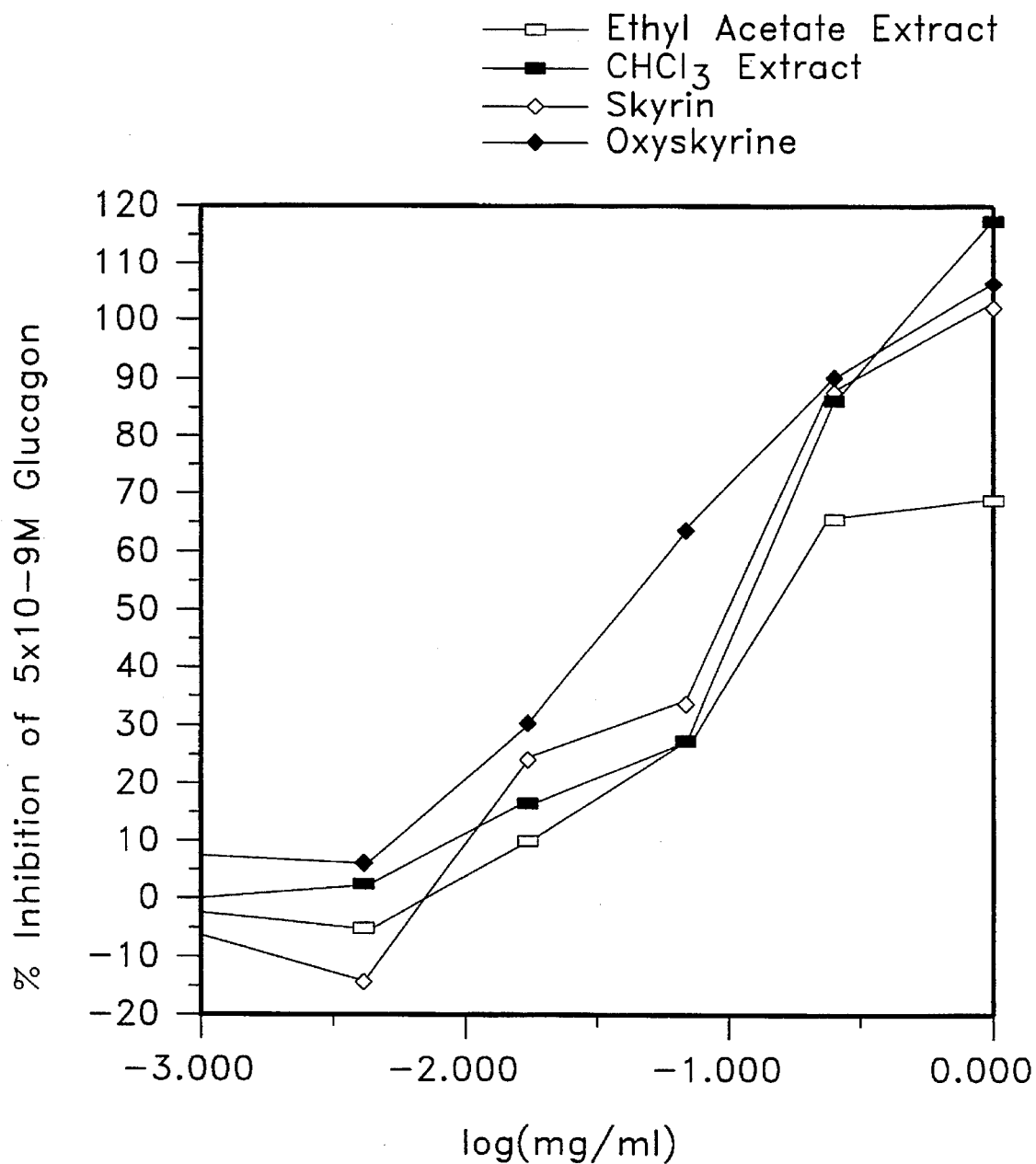
FIG. 7 illustrates that, at fixed glucagon levels, increasing concentrations of two glucagon antagonists of this invention, skyrin and oxyskyrine, increases inhibition of cAMP activity as measured by the Amersham Scintillation Proximity Assay kit.

The cAMP produced in each reaction was determined by assaying 10 µl of each sample using an Amersham Scintillation Proximity Assay kit (Amersham). The results from these assays showed that both oxyskyrine and skyrin inhibited cAMP response to glucagon. FIG. 7 shows that in the presence of a fixed concentration of glucagon, increasing concentrations of skyrin, oxyskyrine and each extract led to an increase in inhibition of cAMP activity.

Example 5

Figure 8:
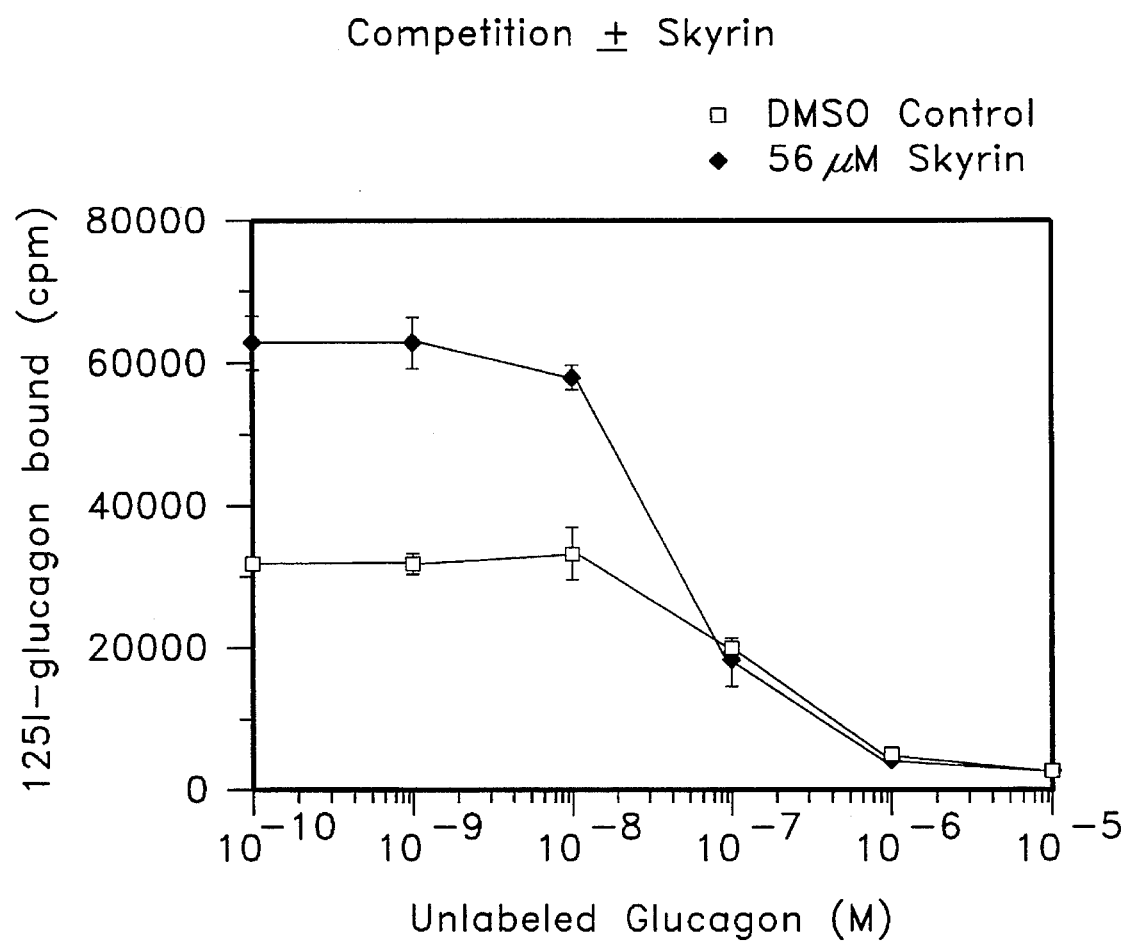
FIG. 8 illustrates that skyrin increases the binding of glucagon to rat liver membranes.

Glucagon binding to rat liver membranes in the presence and absence of skyrin was determined in this experiment. Reactions tubes were prepared, each of which contained 20 µl of serially diluted unlabeled glucagon from $10^{-5}$M to $10^{-10}$ M, 100 µl of 2× binding buffer (100 mM HEPES, pH 7.6), 200 mM NaCl, 2 mM EDTA, 2.0% bovine serum albumin (BSA), 1.0 mg/ml of bacitracin (Sigma Chem. Co.), approximately 0.1 nmoles of $^{125}$I-glucagon (Amersham) in 10 mM acetic acid/0.5% BSA with a specific activity of 2000 Ci/mmole, 20 µl of 56 µM skyrin (dissolved and diluted in DMSO) or DMSO, and water to achieve a final volume of 180 µl. The reaction was initiated by the addition of 0.2 mg of rat liver membranes in 20 µl in water. The reactions were incubated for 30 minutes at 30° C. After incubation the tubes were centrifuged at high speed in a microfuge for 10 minutes at 4° C. The supernatants were discarded, and the radioactivity in the pellets was quantitated with a gamma-counter (the level of radioactivity in a sample indicated the total binding of glucagon to the rat liver membranes). Analysis of data generated from the binding assay demonstrated that skyrin increased binding of glucagon to the rat liver membrane and that the binding was specifically displaced by excess unlabeled glucagon (FIG. 8). Based on this experiment, it is believed that the glucagon antagonists of this invention, including skyrin and skyrin analogs, function as glucagon antagonists by interrupting postglucagon binding events.

From the foregoing, it will be appreciated that, although specific embodiments of the invention have been described herein for purposes of illustration, various modifications may be made without departing from the spirit and scope of the invention. Accordingly, the invention is not limited except as by the appended claims.

We claim:

1. A method for lowering or maintaining blood glucose levels in a patient, comprising administering to the patient a pharmaceutically effective amount of a composition comprising a skyrin analog and a pharmaceutically acceptable carrier or diluent, said skyrin analog having the following structure:

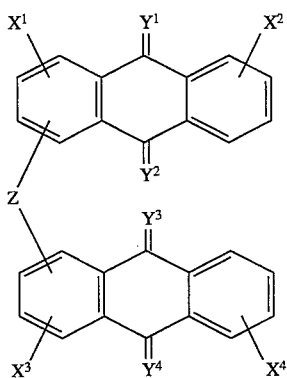

wherein:

X¹, X², X³ and X⁴ are, independently, selected from group consisting of hydrogen, hydroxy, alkyl, alkoxy, halogen, amino, nitro, cyano, sulfhydryl, thioalkyl, trifluoromethane, —O-acyl and —N(R¹)R², where R¹ and R² are, independently, hydrogen or alkyl;

Y¹, Y², Y³ and Y⁴ are, independently, selected from the group consisting of oxygen, sulfur and CH₂; and Z is an optional linker moiety and is selected from the group consisting of alkyl, —O—, —C(=O)—, —O—C(=O)—, —S—, —C(=O)NH—, alkyl-ketone, alkyl-ether and alkyl-ester.

2. The method of claim 1 wherein the skyrin analog has the following structure:

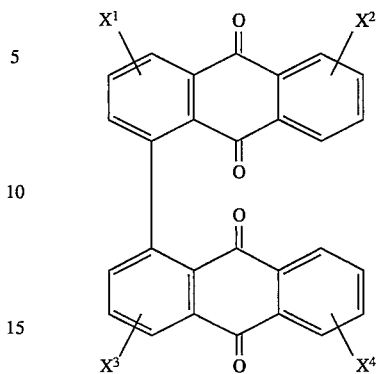

wherein

X¹, X², X³ and X⁴ are, independently, selected from group consisting of hydrogen, hydroxy, alkyl, alkoxy and —O-acyl, wherein —O-acyl is a chemical moiety having the structure —O—C(=O)—R³ or —O—C(=O)—NH—R⁴, where R³ is hydrogen, alkyl or an amino acid having the structure —CH(NH₂)R⁵, and R⁴ is hydrogen, alkyl or an amino acid having the structure —CH(COOH)R⁵, where R⁵ is an amino acid side chain.

3. The method of claim 1 wherein the skyrin analog is oxyskyrine.

4. A method for lowering or maintaining blood glucose levels in a patient, comprising administering to the patient a pharmaceutically effective amount of a composition comprising skyrin and a pharmaceutically acceptable carrier or diluent.

* * * * *